(12) United States Patent
Gruter et al.

(10) Patent No.: US 8,084,267 B2
(45) Date of Patent: Dec. 27, 2011

(54) CORROSION SIMULATOR AND CORRESPONDING METHOD

(75) Inventors: Gerardus Johannes Maria Gruter, Heemstede (NL); Roelandus Hendrikus Wilhelmus Moonen, Amsterdam (NL); Jan Peter de Jong, Amsterdam (NL); David Michael Knowles, Amsterdam (NL)

(73) Assignee: Avantium International B.V., Amsterdam (NL)

( * ) Notice: Subject to any disclaimer, the term of this patent is extended or adjusted under 35 U.S.C. 154(b) by 0 days.

(21) Appl. No.: 12/531,528

(22) PCT Filed: Mar. 19, 2008

(86) PCT No.: PCT/NL2008/000084
§ 371 (c)(1), (2), (4) Date: Dec. 9, 2009

(87) PCT Pub. No.: WO2008/115050
PCT Pub. Date: Sep. 25, 2008

(65) Prior Publication Data
US 2010/0105147 A1   Apr. 29, 2010

(30) Foreign Application Priority Data
Mar. 19, 2007   (EP) .................................... 07075209

(51) Int. Cl.
G01N 27/00 (2006.01)
G01N 21/72 (2006.01)
G01N 21/00 (2006.01)
B01J 19/00 (2006.01)

(52) U.S. Cl. ........ 436/165; 436/164; 436/155; 436/149; 422/129

(58) Field of Classification Search ................. 436/165, 436/164, 155, 149; 422/129
See application file for complete search history.

(56) References Cited

U.S. PATENT DOCUMENTS

| 4,599,217 A | * | 7/1986 | Winston et al. ................. 422/53 |
| 4,711,131 A | * | 12/1987 | Hopkins ......................... 73/799 |
| 5,503,006 A | | 4/1996 | Babaian-Kibala et al. |
| 2005/0076707 A1 | | 4/2005 | Blum et al. |

FOREIGN PATENT DOCUMENTS
WO   WO02092219 A1   11/2002
WO   WO2006107187 A1   10/2006

* cited by examiner

Primary Examiner — Christine T Mui
(74) Attorney, Agent, or Firm — Hoffmann & Baron, LLP (57) ABSTRACT

A laboratory degradation test system for testing degradation of a test specimen in a test fluid flow includes a reactor assembly, which reactor assembly comprises: a reactor vessel, the reactor vessel having a reaction space, an inlet and an outlet and a specimen holder for retaining a test specimen inside the reactor vessel, a heater for heating the reactor vessel, a fluid circulation system generating a test fluid flow over the test specimen, which fluid circulation system comprises: a circulation line which extends between the outlet of the reactor vessel and the inlet of the reactor vessel, which circulation line is arranged outside the reactor vessel, a pump for providing fluid circulation through the circulation line and the reactor vessel, which pump is arranged in the circulation line. The volume available to the test fluid inside the reaction space after insertion of the degradation test specimen is less than or equal to 10 ml.

30 Claims, 5 Drawing Sheets

CORROSION SIMULATOR AND CORRESPONDING METHOD

CROSS-REFERENCE TO RELATED APPLICATIONS

This application is the National Stage of International Application No. PCT/NL2008/000084, filed Mar. 19, 2008, which claims the benefit of European Application No. EP 07075209.2, filed Mar. 19, 2007, the contents of which is incorporated by reference herein.

FIELD OF THE INVENTION

The invention relates to a laboratory degradation test system according to the present invention and to a method for degradation testing according to the present invention.

BACKGROUND OF THE INVENTION

U.S. Pat. No. 5,503,006 discloses a high temperature corrosion simulator. This known corrosion simulator comprises a reactor vessel or an array of reactor vessels which can be arranged in series. In such a reactor vessel, a corrosion coupon or a different kind of corrosion probe can be introduced. Through the reactor vessel or reactor vessels, a high temperature test fluid, which is at least suspected to induce corrosion, is circulated. The simulator further comprises a plug for influencing the flow pattern of the test fluid through the reactor vessel. Such a plug can be provided with a heat exchanger.

The known corrosion simulator and method has the disadvantage that the test fluid is kept at a high temperature throughout the entire execution of the test. Many relevant test fluids, such as crude oil or fractions thereof, tend to respond to this by a change in properties, which change has an undesired effect on the test results.

SUMMARY OF THE INVENTION:

The object of the invention is to provide an improved laboratory degradation test system and an improved method for degradation testing.

This object is achieved by the laboratory degradation test system according to the present invention and by the method for degradation testing according to the present invention.

The test system according to the invention is characterised in that the volume available to the test fluid in the reaction space after insertion of the degradation test specimen is less than or equal to 10 ml. A small volume of test fluid responds faster to heating than a larger volume of test fluid. By limiting the volume of test fluid that can be contained in the reactor vessel, more in particular in the reaction space of the reactor vessel, heating the reactor vessel results in an effective heating of the test fluid that is present in the reactor vessel. This way, the general temperature in the circulation system at some distance from the outlet of the reactor vessel ("the circulation temperature") can be kept relatively low, while still a high temperature of the test fluid in the reactor vessel can be reached. The circulation temperature generally is about equal to the temperature at which the test fluid enters the reactor vessel, unless additional heating is applied in the circulation line.

When the test fluid leaves the reactor vessel, it re-enters the circulation line at a temperature that is more or less equal to the reaction temperature. Due to the small volume of the heated test fluid, the temperature of the test fluid that was heated by the reactor vessel drops relatively quickly to the circulation temperature without the need for additional active cooling. So, in general no additional technical provisions for cooling the test fluid after it has left the reactor vessel, such as providing a cooling unit, have to be made. Due to the small heated volume and the rapid cooling, the circulation temperature will be substantially equal to the volume based average temperature of the test fluid in the circulation system, if no further heating or cooling takes place in the circulation system.

In order to make use of this effectively, it is preferred that the volume available to the test fluid inside the reaction space after insertion of the degradation test specimen is less than or equal to 10%, more preferably less than or equal to 5%, of the total the volume available to the test fluid in the reactor vessel assembly and the circulation system together.

In a possible embodiment, the flow rate of the test fluid in the circulation line is kept low, preferably less than 10 ml/min, more preferably less than or equal to 1 ml/min. By applying such a low flow rate of the test fluid, the residence time of the test fluid in the reactor vessel can be relatively long. This allows effective heating of the test fluid by the reactor vessel. A small cross sectional area of the space inside the reaction space that is available to the test fluid can provide a suitable mass transport over the test specimen.

In a preferred embodiment, the total volume available for the test fluid in the test system, more in particular in the reactor assembly and in the fluid circulation system together, is limited, preferably to 500 ml, more preferably to 50 ml. Such a small scale test system makes that a limited quantity of test fluid suffices for carrying out a degradation test. This is particularly advantageous when only a small quantity of test fluid is available, for example when the test fluid has to be obtained by a time consuming and/or energy consuming process. This is for example the case when the test fluid is a fraction of crude oil that has to be obtained by distillation. Moreover, small scale test assemblies allow fast performance of many tests.

It is envisaged that the test system comprises a plurality of reactor vessels. A number of possible embodiments are possible with this option. First, an embodiment is envisaged in which a plurality of reactor vessels is arranged in parallel. In that case, the circulation line comprises an inlet manifold for distributing the total test fluid flow over the individual reactor vessels. Such a manifold may comprise a flow splitter, which for example comprises a plurality of capillary tubes or orifices. In this embodiment, the circulation line also comprises an outlet manifold, which collects the test fluid leaving the individual reactor vessels in the circulation line. This embodiment allows parallel degradation tests to be carried out in a single test system. All reactor vessels will usually be fed with the same test fluid, but the test conditions in the individual reactor vessels may be varied. For example, different temperatures or pressures may exist in the different reactor vessels, or test specimens of different materials may be arranged in the different reactor vessels.

Second, an embodiment is envisaged in which a plurality of reactor vessels is arranged in series.

Third, an embodiment is envisaged in which not only a plurality of reactor vessels is provided, but also a plurality of circulation lines. Each circulation line can be associated with a single reactor vessel, but it is also envisaged that multiple reactor vessels are connected to a single circulation line. The use of a plurality of circulation lines allows the parallel use of different test fluids.

In an advantageous embodiment, the test system also comprises at least one reactor block, in which at least one reactor vessel can be arranged. In a preferred embodiment, the reactor block is a temperature controlled reactor block. In that case, the reactor block can be used to heat the reactor vessel or the reactor vessels that are present in the reactor block.

In an advantageous embodiment, the reactor vessel is made from a non-metallic material, for example quartz or glass. This is particularly advantageous in corrosion testing, because it avoids contact of the—often metallic—test specimen with an other metal object. Such metal-to-metal contact between two different metals may induce galvanic corrosion, which would influence the test results in an undesired way.

In an advantageous embodiment, a reactor block with glass or quartz reactor vessels according to WO02/092219 is used.

In a further advantageous embodiment, a pressure control system according to WO2006/107187 is used for controlling the pressure in de reactor vessel or reactor vessels.

In an advantageous embodiment, the specimen holder is adapted to hold a cylindrical test specimen, such as a test specimen in the form of a rod or wire or a hollow cylinder. Such test specimens allow the use of small scale reactor vessels. In case of a hollow test specimen, the test fluid can be made to flow through the test specimen, around the test specimen or both.

In a further possible embodiment, the specimen holder allows to impose a mechanical stress, for example a shear stress or tensile stress, on the test specimen. A shear stress can for example be imposed by twisting the one end of the test specimen relative to the other end. The specimen holder can then be adapted to maintain this twisted position of the test specimen during testing. This way, the occurrence stress corrosion cracking can be tested. This is particularly advantageous because it is hardly possible to predict the occurrence of stress corrosion cracking on the basis of a theoretical approach.

The test system according to the invention can be used for corrosion testing. The corrosion resistance of a specific metal against a specific test fluid can be tested, if desired under specific process conditions. When an embodiment is used that comprises a plurality of reactor vessels, in a short period of time much data can be gathered, for example by applying different process conditions in the different reactor vessels, by using test specimens of different materials and/or by applying different test fluids.

The test system can also be used for testing the effectiveness of corrosion inhibitors.

The test system can also be used for testing the degradation of non-metallic test specimens in relation to a specific environment. For example, the swelling of polymer test specimens in a specific test fluid can be tested. Also, the dissolution of components of materials is a specific environment can be tested.

After or during the contacting of the test specimen by the test fluid, degradation analysis is performed. Such analysis can involve any known kind of relevant analysis. In the case of testing for corrosion, such degradation analysis can for example involve weighing of the test specimen before and after the test, measuring the electrical conductivity of the test specimen and/or of the test fluid, measuring the thermal conductivity of the test specimen, radiological testing, and/or measuring the concentration of corrosion products in the test fluid.

In the case of stress corrosion testing, crack detection, such as eddy current analysis or magnaflux, can be used as an appropriate degradation analysis.

BRIEF DESCRIPTION OF THE DRAWINGS

The invention will be described in more detail below under reference to the drawings, in which in a non-limiting manner exemplary embodiments of the invention will be shown.

The drawings show in.

DETAILED DESCRIPTION OF THE INVENTION

Figure 1:
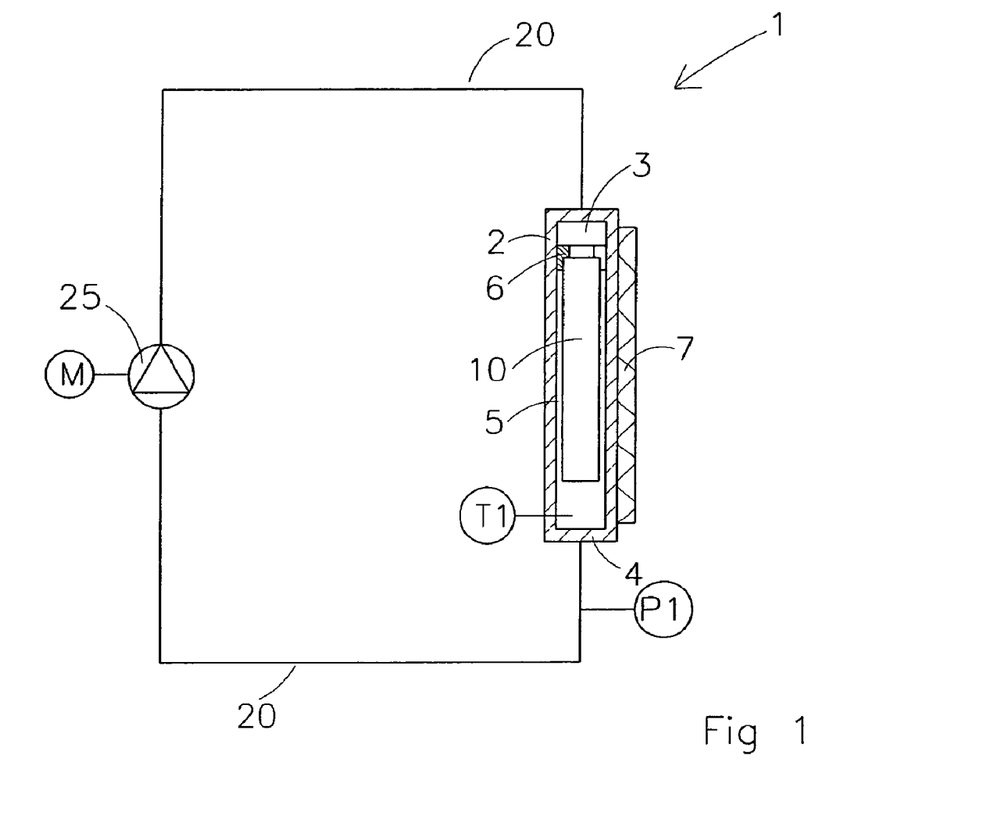
FIG. 1—a first embodiment of a laboratory test system according to the invention, FIG. 2—a second embodiment of a laboratory test system according to the invention, FIG. 3—a third embodiment of a laboratory test system according to the invention, FIG. 4—a fourth embodiment of a laboratory test system according to the invention, FIG. 5—a part of a fifth embodiment of a laboratory test system according to the invention, FIG. 6—exemplary embodiments of a specimen holder for stress corrosion testing.

FIG. 1 shows a first embodiment of a laboratory test system 1 according to the invention.

FIG. 1 shows a reactor vessel 2, which has an inlet 3, an outlet 4 and a reaction space 5. The reactor vessel can be heated by heater 7. Heater 7 can be any kind of known heater for this purpose, like a heat exchanger or an electrical resistance wire, which is wound around the reactor vessel 2. Alternatively, the reactor vessel 2 can be heated by means of a temperature controlled reactor block, in which the reactor vessel 2 is arranged.

The reactor vessel 2 is further provided with a test specimen holder 6 for retaining a degradation test specimen 10 in the reaction space. The test specimen holder can be any structure that retains a test specimen 10 in the reaction space. The test specimen holder can be for example a clamp that holds the test specimen, but also a filter or frit that prevents the test specimen from being dragged along by the test fluid. In addition or as an alternative for retaining ferrous metal test specimens, the test specimen holder can be a magnetic holder, being arranged either inside or outside the reactor vessel.

The test system 1 further comprises a fluid circulation system that comprises a circulation line 20. In this example, a mechanical pump 25, driven by motor M, is provided in the circulation line 20. Instead of a mechanical pump, also an other type of pump can be provided, such as a thermosifon. A thermosifon has the advantage that it does not comprise moving parts so that it is less susceptible to wear and therefore needs less maintenance.

The test system 1 also comprises a temperature controller T1 and a pressure controller P1.

When using the embodiment of FIG. 1 for degradation testing, first a degradation test specimen 10 is arranged in the test specimen holder 6. The test specimen can for example be a corrosion coupon. The test specimen 10 can in principle have any suitable shape. Corrosion coupons are usually flat, rectangular pieces of metal, but they can take any other suitable form as well, for example cylindrical.

In the test system according to the invention, it is advantageous to use elongated, slender cylindrical test specimens, for example rod-shaped or wire-shaped test specimens. Reactor vessels generally have a cylindrical shape. When a cylindrical test specimen is placed in the reactor vessel, the diameter of the test specimen can be chosen such that just a narrow space around the test specimen is present through which the test fluid can flow through the reaction space during testing.

For example a combination of a cylindrical reactor vessel with an internal diameter of 2 mm with a test specimen having an outer diameter of 1.6 mm has in practice proven to be suitable. An other proven suitable combination is a cylindrical reactor vessel with an internal diameter of 4 mm with a cylindrical test specimen having and outer diameter of 3.4 mm.

Degradation testing in general, and corrosion testing in particular, requires a certain size of the surface to be exposed to the test medium. With the sizes of the cylindrical test specimens as mentioned in the previous paragraph, the required surface size can be obtained by choosing the length of the specimen. In practice, lengths of 5 cm (resulting in a surface size of 251 mm$^2$ for the 1.6 mm diameter specimen and of 534 mm$^2$ for the 3.4 mm diameter specimen) and 20 cm (resulting in a surface size of 1005 mm$^2$ for the 1.6 mm diameter specimen and of 2135 mm$^2$ for the 3.4 mm diameter specimen) have proven suitable.

When the test specimen 10 has been inserted in the reactor vessel 2, the test fluid is introduced in the circulation line 20. This can be done in any suitable way. On introduction of the test fluid, the system is de-aerated.

Usually, it will be necessary to carry out the degradation test at an elevated temperature. To that end, the test system is provided with a heater 7 for heating the reactor vessel 2. After filling the test system with the test fluid, the reactor vessel 2 is heated until it achieves the desired temperature. If it is desired to carry out the degradation test at an elevated pressure, a suitable pressurisation of the test system is carried out, for example using a source of nitrogen under pressure.

Energising the pump 25 results in a circulation of test fluid through the circulation line 20 and the reactor vessel 2. The test fluid flows over the test specimen 10 in the longitudinal direction of the test specimen, so it is ensured that the entire surface of the test specimen 10 is in contact with the test fluid.

The volume inside the reactor vessel 2 that is available to the test fluid is far smaller than the total volume available for the test fluid inside the test system. In a typical embodiment that has proven to be suitable in practice, the total volume available to the test fluid can be about 20 to 25 ml, while the volume available to the test fluid in the reactor vessel 2 is 0.2 to 0.5 ml.

Especially in combination with a small overall flow rate of for example 1 ml per minute, the test fluid is heated by the reactor vessel 2 on passing through it. Because of the small volume of the test fluid inside the reactor vessel 2, a relatively small heat flux is sufficient to obtain a relatively large increase in temperature of the test fluid in the reactor vessel 2. With the parameters mentioned in the previous paragraph and in this paragraph, a temperature increase of a test fluid being crude oil or a fraction from 80° C. in the circulation line to 300° C. in the reactor vessel 2 has been obtained.

The test system 1 according to the invention can be used at both elevated temperatures (up to 1050° C.) and/or elevated pressures (up to 400 barg).

As soon as the test fluid leaves the reactor vessel 2 via the outlet 4, the test fluid rapidly cools from the reaction temperature to the circulation temperature. The rapid cooling is due to the small volume of the test fluid that is heated by the reactor vessel. In general, additional means for forced cooling are not necessary.

When the test system 1 is used for corrosion testing, the test fluid can be any suitable medium such as $H_2$, $H_2S$, air, $NH_3$, crude oil or fractions thereof, a mixture of oil and water, a mixture of oil and natural gas, a mixture of oil and steam, steam, salt steam, sour steam, HCl, salt water, a mixture of oil and salt water, condensate, an mixture of water and condensate and so on.

The test system 1 according to the invention can also be used to test the effectiveness of corrosion inhibitors. In that case, an appropriate quantity of corrosion inhibitor is added to the test fluid.

After contacting the test specimen 10 with the test fluid for the duration of the test, the test specimen can be subjected to further analysis, such as weighing or (electron)microscopic examination. During the test itself, analysis can be carried out too, for example by means of concentration measurements.

In a non-shown variant to FIG. 1, the test fluid is not circulated though the circulation line 20, but transferred from a source, via the reaction space to a waste vessel.

Figure 2:
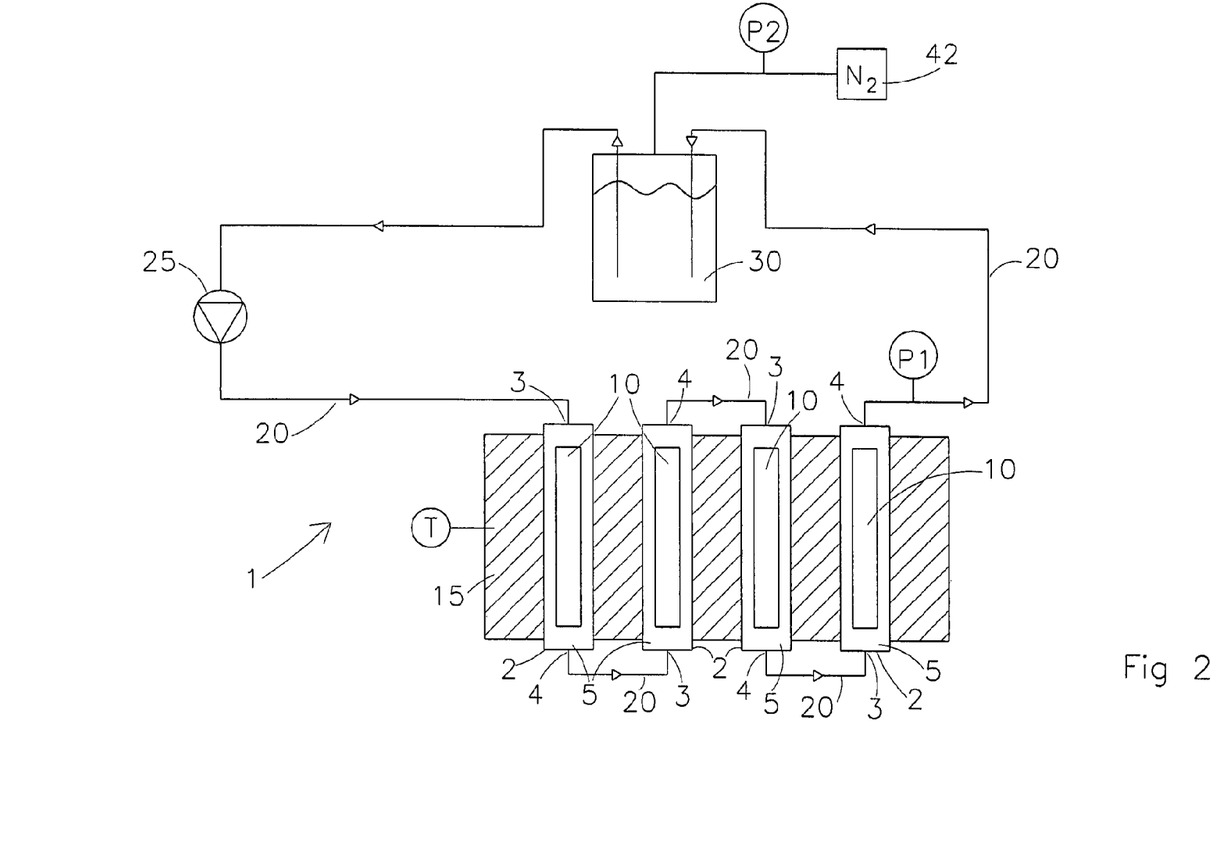

FIG. 2 shows a second embodiment of the test system 1 according to the invention. This second embodiment is largely based on the embodiment of FIG. 1.

In the embodiment of FIG. 2, a plurality of reactor vessels 2 is present. In the example of FIG. 2, four reactor vessels 2 are provided. The reactor vessels 2 are arranged in a reactor block 15. In the embodiment of FIG. 2, the reactor block 15 is provided with temperature control T, so that by means of the reactor block 15, the temperature of the reactor vessels can be controlled.

In the example of FIG. 2, a reservoir 30 is present in the circulation system. A pressurised nitrogen source N2 provides a desired pressure in the reservoir. To this end, a pressure gauge P2 is provided. A reservoir of the type shown in the embodiment of FIG. 2 can also be applied in the other described embodiments.

In the embodiment of FIG. 2, the reactor vessels 2 are arranged in series. This way, several tests can be carried out simultaneously. A practical case in which it is advantageous to arrange the reactor vessels 2 in series is when a situation in a plant such as a refinery in which different types or materials are used for the equipment is to be simulated. In that case, test specimens of those different materials, in the order in which they are present in the plant as seem in the direction of the product flow, can be arranged in the reactor vessels 2.

In the embodiment of FIG. 2, the circulation line 20 is divided into several parts: one part extending from the reservoir 30, via the pump 25 to the inlet 3 of the first reactor vessel 2, the parts between the outlet 4 of one reactor vessel 2 and the inlet 3 of the adjacent reactor vessel 2, and the part between the outlet 4 of the last reactor vessel 2 (as seen in the direction of the fluid flow).

Pressure controller P1 is provided to control the pressure in the reactor vessels 2.

Figure 3:
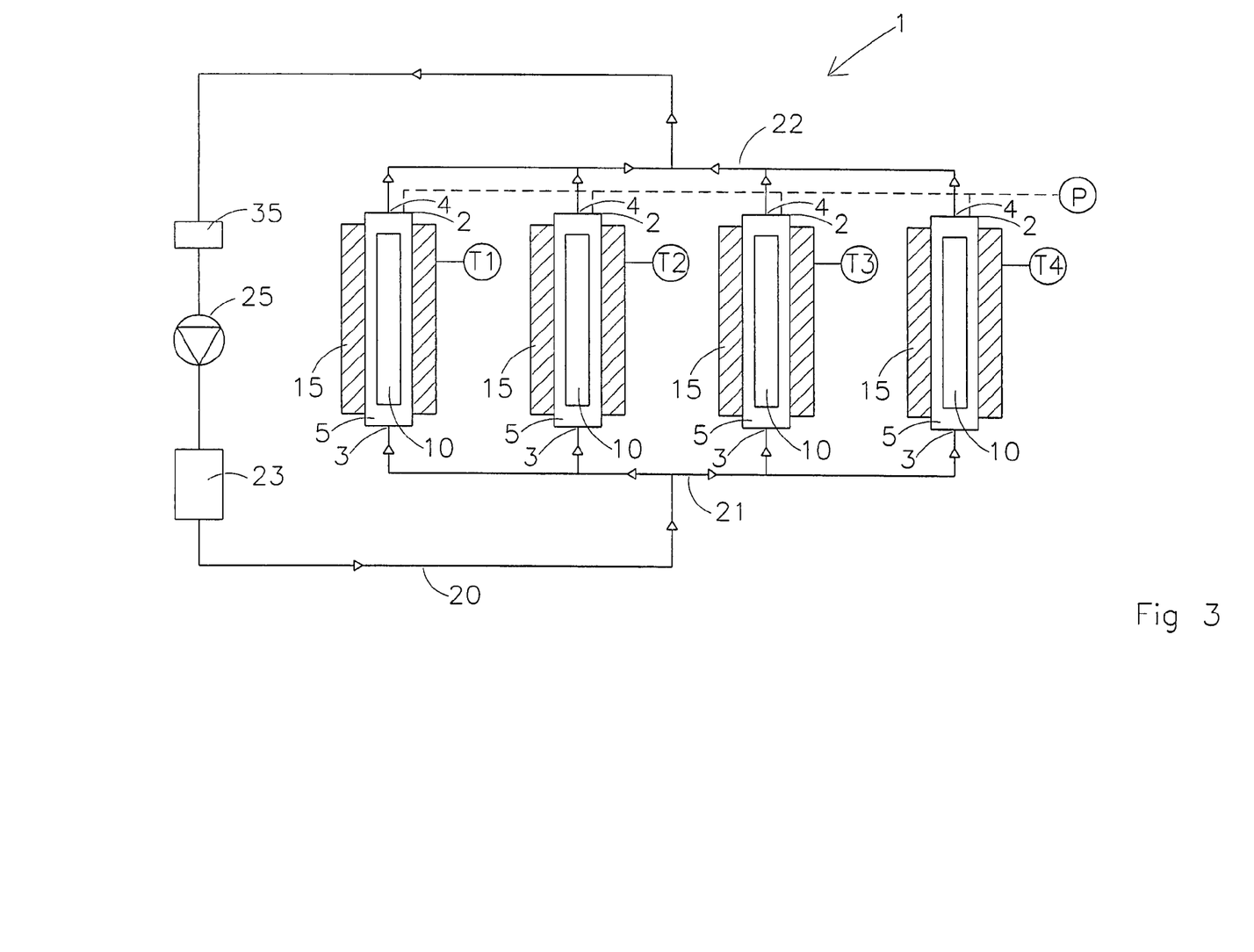

FIG. 3 shows a third embodiment of the test system 1 according to the invention. This third embodiment is largely based on the embodiment of FIG. 1.

In the embodiment of FIG. 3, a plurality of reactor vessels 2 is present. In the example of FIG. 3, four reactor vessels 2 are provided. In the embodiment of FIG. 3, the reactor vessels 2 are arranged in parallel.

In the example of FIG. 3, each reactor vessel 2 is arranged in a separate reactor block 15. Each reactor block 15 is provided with a heater, for example in the form of channels through the reactor block through which a heating medium such as hot air or thermic oil can flow. The advantage of this set up is that each reactor vessel 2 can be given a different temperature, without influencing the temperature in the other reactor vessels. The temperature in the different reactor blocks 15 is controlled by separate temperature controllers T1, T2, T3, T4. In a variant of this embodiment, a plurality of reactor vessels 2 is arranged in each reactor block 15.

In order to provide all reactor vessels 2 with test fluid, the circulation line 20 is provided with an inlet manifold 21.

Outlet manifold 22 collects the test fluid form the reactor vessels 2 in the circulation line 20.

In the embodiment of FIG. 3, a pressure control system P according to WO2006/107187 is used for controlling the pressure in the reactor vessels.

In this example, the circulation line 20 is provided with a connection point 35. Through this connection point 35, test fluid can be introduced into and/or evacuated from the test system 1. Preferably, the connection point is further provided with means for de-aerating and/or purging the test system 1. This connection point 35 can be of any suitable type, and can for example include a septum or a weldolet with a valve. A connection point of the type shown in the embodiment of FIG. 3 can also be applied in the other described embodiments.

In the example of FIG. 3 optionally an additional heater 23 is provided in the circulation line 20. This heater 23 can be used for maintaining a desired temperature of the test fluid in the circulation line. This is especially useful in case the test fluid has a high viscosity at room temperature, such as crude oil. When using crude oil as a test fluid, using heater 23 to maintain a circulation temperature of about 80° C. in the circulation line has proven a suitable compromise between the viscosity and the risk of degradation of the oil. A heater 23 of the type shown in the embodiment of FIG. 3 can also be applied in the other described embodiments.

Figure 4:
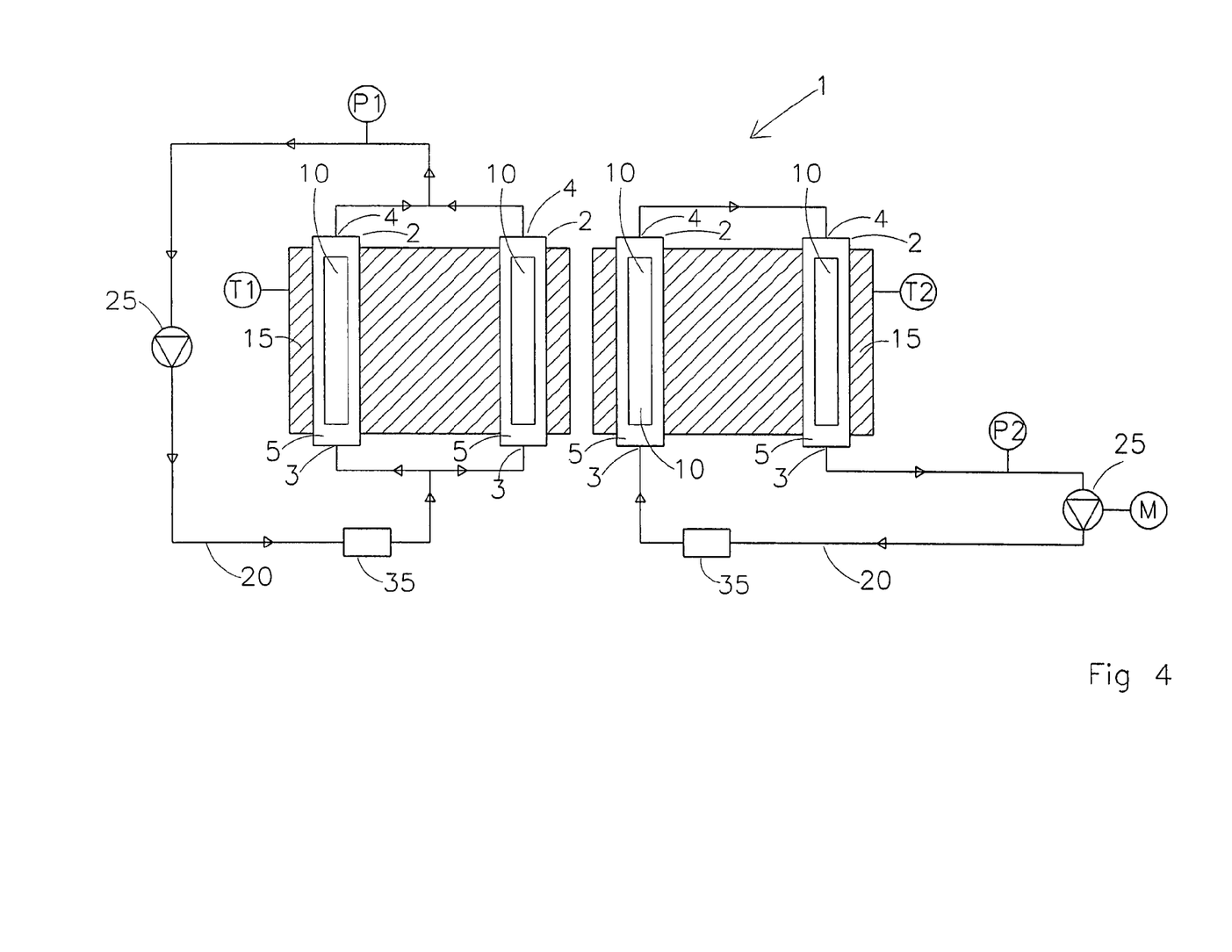

FIG. 4 shows a fourth embodiment of the test system 1 according to the invention. This fourth embodiment is largely based on the embodiment of FIG. 1 and comprises a combination of embodiments similar to those of FIG. 2 and FIG. 3.

Figure 5:
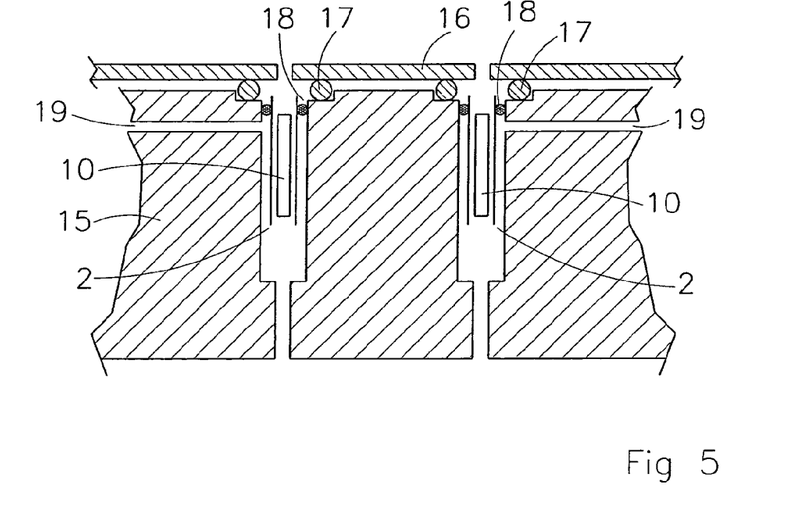

FIG. 5 shows a part of a fifth embodiment of a test system 1 according to the invention.

In the embodiment of FIG. 5, a reactor block 15 with glass or quartz reactor vessels 2 according to WO02/092219 is used. The reactor block 15 has a cover 16 and seals 17, 18. As an optional feature, additional channels 19 are provided in the reactor block 15 as shown in FIG. 5. These channels can be used to provide a pressure in the annular space between the wall of the reactor vessel and the wall of the recess of the reactor block that contains the reactor vessel 2, in order to prevent test fluid from entering this annular space. For example if crude oil is used as a test fluid, the oil in this annular space soils the system and can make the reactor vessel hard to remove from the reactor block. Also, such oil will degenerate due to the extended stay at high temperature. In a system without circulation, in which the test fluid flows from a source via the reactor vessel to a waste collector, the additional channels can be used to dilute the reactor effluent, for example in order to speed up the removal of the reactor effluent from the reaction space.

In the embodiment of FIG. 5, the wall of the reactor vessels 2 are arranged at a distance from the wall of the recess in the reactor block 15 in which the particular reactor vessel 2 is accommodated. Due to this distance, the pressure outside the reactor vessel 2 is the same as the pressure inside the reactor vessel 2. This allows the use of reactor vessels 2 of a relatively brittle material such as glass or quartz even for high pressure tests.

For corrosion testing, it is advantageous to use non-metallic reactor vessels 2, because this way metal-to-metal contact between the test specimen 10 and the reactor vessel 2 is avoided. Such metal-to-metal contact could be the source of galvanic corrosion, which would influence the outcome of the corrosion tests in an undesirable way.

FIG. 6 shows two exemplary embodiments of a specimen holder suitable for stress corrosion testing.

Figure 6A:
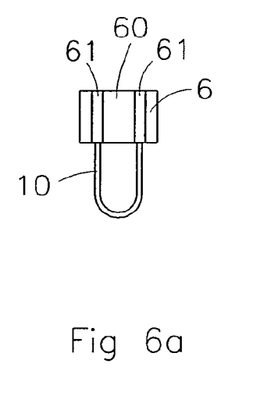

In the specimen holder 6 according to FIG. 6A, a plug 60 with channels 61 is provided. The plug 60 can be arranged in a reactor vessel 2. The plug 60 is then kept in place by the friction between the wall of the reactor vessel 2 and the plug 60 itself. Channels 61 are provided to allow test fluid to pass by the plug 60.

In the specimen holder 6 according to FIG. 6A a test specimen 10 in the form of a bend wire is arranged. By bending the test specimen 10, a tensile stress is induced upon the test specimen 10. Also non-wire shaped test specimens 10 can be bend and used in the specimen holder 6 of FIG. 6A.

Figure 6B:
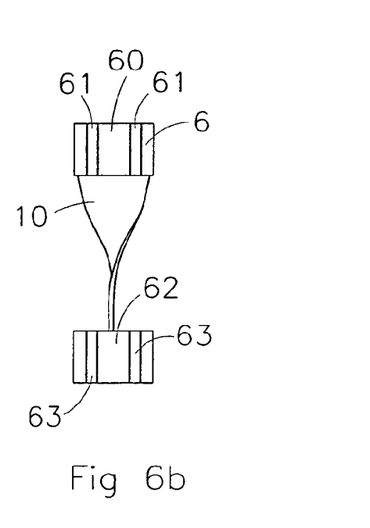

In the example of FIG. 6B, two plugs 60, 62 are provided. The plugs 60,62 are provided with channels 61,63 for allowing the test fluid to pass by the plugs.

In the specimen holder 6 according to FIG. 6B, the test specimen 10 is twisted in order to introduce shear stress into the test specimen 10. Test specimens 10 of any shape, including rod-shaped or wire-shaped test specimens 10 can be twisted in order to obtain shear stress.

The use of test specimen holders 6 of the kind shown in FIG. 6 is not limited to stress corrosion testing. Such specimen holders 6 can be used in any case wherein it is suspected that material stresses in the test specimen 10 are a factor of influence in the degradation behaviour.

The invention claimed is:

1. Laboratory degradation test system for testing degradation of a test specimen in a test fluid flow,
the test system comprising:
a reactor assembly, which reactor assembly comprises:
a reactor vessel, the reactor vessel having a reaction space, an inlet and an outlet and a specimen holder for containing a test specimen in the reaction space,
a heater for heating the reactor vessel,
a fluid circulation system for generating a test fluid flow through the reactor vessel, to which flow the test specimen is exposed, which fluid circulation system comprises:
a circulation line which extends between the outlet of the reactor vessel and the inlet of the reactor vessel, which circulation line is arranged outside the reactor vessel,
a pump for providing fluid circulation through the circulation line and the reactor vessel, which pump is arranged in the circulation line,
and a test specimen,
wherein the volume available to the test fluid inside the reaction space after insertion of the degradation test specimen is less than or equal to 10 ml.

2. Degradation test system according to claim 1, wherein the volume available to the test fluid inside the reaction space after insertion of the degradation test specimen is less than or equal to 1 ml.

3. Degradation test system according to claim 1, wherein the volume available to the test fluid in the reactor vessel assembly and the circulation system together is less than or equal to 500 ml.

4. Degradation test system according to claim 3, wherein the volume available to the test fluid in the reactor vessel assembly and the circulation system together is less than or equal to 50 ml.

5. Degradation test system according to claim 1, wherein the volume available to the test fluid inside the reactor after insertion of the degradation test specimen is less than or equal to 5% of the total the volume available to the test fluid in the reactor vessel assembly and the circulation system together.

6. Degradation test system according to claim 1, wherein the test system comprises a plurality of reactor vessels that are arranged in parallel.

7. Degradation test system according to claim 1, wherein the test system comprises a plurality of reactor vessels that are arranged in series.

8. Degradation test system according to claim 1, wherein the test system comprises a plurality of reactor vessels, a plurality of circulation lines and a plurality of pumps, each reactor vessel being associated with a particular circulation line and a particular pump, preferably the volume available to the test fluid inside a specific combination of a reactor vessel, its associated circulation line and its associated pump being less than or equal to 500 ml.

9. Degradation test system according to claim 1, wherein the pump is adapted to generate a flow rate of the test fluid of less than 10 ml/min.

10. Degradation test system according to claim 1, wherein the fluid circulation system further comprises a reservoir for holding a quantity of test fluid.

11. Degradation test system according to claim 1, wherein the test system further comprises a reactor block for accommodating at least one reactor vessel.

12. Degradation test system according to claim 11, wherein the reactor block accommodates the heater for heating the reactor vessel.

13. Degradation test system according to claim 1, wherein the reactor vessel is made of a non-metallic material.

14. Degradation test system according to claim 13, wherein the reactor vessel is made of quartz or glass.

15. Degradation test system according to claim 1, wherein the specimen holder is adapted to retain an elongated cylindrical test specimen, preferably a slender, rod-shaped or wire-shaped test specimen.

16. Degradation test system according to claim 1, wherein the specimen holder is adapted to hold the test specimen under a mechanical stress, a shear stress or tensile stress.

17. Degradation test system according to claim 1, wherein the reaction space is cylindrical and wherein the inlet of the reactor vessel and the outlet of the reactor vessel are arranged at opposed axial ends of the reaction space and wherein a slender elongated test specimen is arranged axially in said reaction space.

18. A method for testing degradation of a test specimen in a test fluid flow comprising:
  utilizing the test system according to claim 1 for corrosion testing.

19. Method for assessing degradation properties of a degradation test specimen in a test fluid flow, which method comprises the following steps:
  providing a test system according to claim 1,
  arranging a degradation test specimen in a specimen holder and arranging said test specimen inside the reactor vessel,
  introducing a quantity of test fluid into the test system, the volume of the test fluid preferably being less than or equal to 500 ml,
  heating the reactor vessel to the test temperature,
  energising the pump during a period of time such that a test fluid flow is generated such that the test fluid flows over the surface of the test specimen, and
  performing a degradation analysis.

20. Method according to claim 19, wherein the degradation analysis includes weighing of the test specimen.

21. Method according to claim 19, wherein the degradation analysis includes measuring the concentration of reaction products in the test fluid.

22. Method according to claim 19, wherein the degradation analysis includes measuring the conductivity of the test fluid and/or the test specimen.

23. Method according to claim 19, wherein an apparatus according to claim 6 is provided, and wherein at least one reactor vessel is provided with a different temperature than an other reactor vessel.

24. Method according to claim 19, wherein an apparatus comprising a test system comprising:
  a reactor assembly, which reactor assembly comprises:
    a reactor vessel, the reactor vessel having a reaction space, an inlet and an outlet and a specimen holder for containing a test specimen in the reaction space,
    a heater for heating the reactor vessel,
  a fluid circulation system for generating a test fluid flow through the reactor vessel, to which flow the test specimen is exposed, which fluid circulation system comprises:
    a circulation line which extends between the outlet of the reactor vessel and the inlet of the reactor vessel, which circulation line is arranged outside the reactor vessel,
    a pump for providing fluid circulation through the circulation line and the reactor
  vessel, which pump is arranged in the circulation line, and a test specimen,
  wherein the volume available to the test fluid inside the reaction space after insertion of the degradation test specimen is less than or equal to 10 ml;
  wherein the test system comprises a plurality of reactor vessels, a plurality of circulation lines and a plurality of pumps, each reactor vessel being associated with a particular circulation line and a particular pump, preferably the volume available to the test fluid inside a specific combination of a reactor vessel, its associated circulation line and its associated pump being less than or equal to 500 ml; and
  wherein in at least one specific combination of a reactor vessel, its associated circulation line and its associated pump a different test fluid is introduced than in an other combination of a reactor vessel, its associated circulation line and its associated pump.

25. Method according to claim 19, wherein the test fluid is preheated before entering the reactor vessel.

26. Method according to claim 19, wherein the circulation temperature of the test fluid is preferably less than or equal to 100° C.

27. Method according to any of the claims 19-25, wherein the temperature of the reactor vessel is at least 250° C.

28. Method according to claim 19, wherein the difference between the circulation temperature and the temperature of the reactor vessel is at least 150° C.

29. Method according to claim 19, wherein the flow rate of the test fluid is less than 10 ml/min 30. Method according to claim 19, wherein the test system comprising:
  a reactor assembly, which reactor assembly comprises:
    a reactor vessel, the reactor vessel having a reaction space, an inlet and an outlet and a specimen holder for containing a test specimen in the reaction space,
    a heater for heating the reactor vessel, a fluid circulation system for generating a test fluid flow through the reactor vessel, to which flow the test specimen is exposed, which fluid circulation system comprises:
    a circulation line which extends between the outlet of the reactor vessel and the inlet of the reactor vessel, which circulation line is arranged outside the reactor vessel,
    a pump for providing fluid circulation through the circulation line and the reactor vessel, which pump is arranged in the circulation line, and a test specimen, wherein the volume available to the test fluid inside the reaction space after insertion of the degradation test specimen is less than or equal to 10 ml;

wherein the specimen holder is adapted to hold the test specimen under a mechanical stress, a shear stress or tensile stress; and wherein the degradation analysis includes crack detection.

* * * * *